United States Patent [19]

Fuchs

[11] 4,384,127

[45] May 17, 1983

[54] PROCESS FOR SYNTHESIS OF OPTICALLY PURE PROSTAGLANDIN $E_2$ AND ANALOGS THEREOF

[75] Inventor: Phillip L. Fuchs, West Lafayette, Ind.

[73] Assignee: Purdue Research Foundation, West Lafayette, Ind.

[21] Appl. No.: 251,844

[22] Filed: Apr. 8, 1981

[51] Int. Cl.³ .............................................. C07D 303/34
[52] U.S. Cl. ...................................... 549/546; 560/121
[58] Field of Search .................... 260/348.43; 549/546

*Primary Examiner*—Norma S. Milestone
*Attorney, Agent, or Firm*—E. Janet Berry

[57] ABSTRACT

The invention comprises a multi-step synthesis of l(−) prostaglandin $E_2$. The special features of the synthesis include: (1) a triply-convergent conjugate-addition and alkylation reaction involving the 1,4-addition of a chiral vinyl lithium reagent to a chiral vinylsulfone to produce a sulfone-stabilized anion. This anion is alkylated in situ to produce the basic prostaglandin skeleton structure, which is then subjected to (2) an efficient peracid oxidation of a secondary amine to a $\beta$-silyloxy oxime; and (3) an alkali-catalyzed 1,4-elimination of an $\alpha$-sulfonyl oxime to produce a vinyl nitroso intermediate. This intermediate is treated with borohydride to give a stereospecific 1,4-reduction which yields the bis-silyloxy oxime of l(−)$PGE_2$. Hydrolysis of the oxime, with concurrent cleavage of the silyloxy protecting groups, affords l(−)$PGE_2$.

2 Claims, No Drawings

PROCESS FOR SYNTHESIS OF OPTICALLY PURE PROSTAGLANDIN E₂ AND ANALOGS THEREOF

FIELD OF INVENTION

The invention relates broadly to multiple step chemical processes for production of certain selected, optically active prostaglandins, especially prostaglandins of the $PGE_2$ type and includes also production of certain of their analogs and related compounds. Of special importance is the novel synthesis of prostaglandin $E_2$ ($PGE_2$ 1) useful both as an end product and as an intermediate to produce other optically active prostaglandins and related products and intermediates. It is also contemplated that the invention comprises one or more individual and novel process steps as well as certain subcombinations of process steps whereby it is possible to use the improved methods for synthesis of optically active prostaglandins and also for production of other compounds.

BACKGROUND

Both the chemistry and various biological activities of prostaglandin $E_2$ (1) and prostaglandin $F_2$ (2) as well as other compounds having the prostaglandin structure have been studied in recent years. The synthesis of prostacyclin (3) as well as many of its analogs have received considerable attention and study especially because of their potency as inhibitors of blood platelet aggregation. An easy conversion of prostaglandin $E_2$ to prostacyclin (1→2→3) makes $PGE_2$ (1) and its analogs especially valuable for the future preparation of prostacyclin congeners as very good candidates for future study.

In particular, the compound prostaglandin $E_2$ ($PGE_2$ 1) is an important intermediate for preparation of other prostaglandins and occupies a position of great importance with the entire group of prostaglandin compounds.

The formula for this important intermediate is as follows:

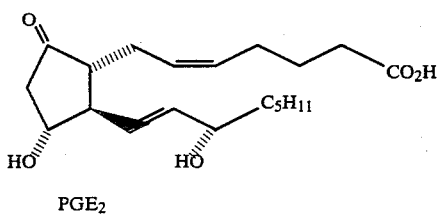

PGE₂ (1)

Of particular importance is its role as a convenient intermediate into other, structurally different, prostaglandins such as $PGF_2 \alpha$ 2, and $PGI_2$ 3. Among these products, all of which are known, is the compound $PGI_2$ 3 and some of its analogs which have been found to be very effective as inhibitors of blood platelet aggregation. These compounds and their analogs are also being tested for activity in controlling blood pressure. They are also currently under study for various industrial uses including, but not limited to, the pharmaceutical field.

SUMMARY OF THE INVENTION

There has now been discovered a novel and advantageous multi-step synthesis of $PGE_2$ involving a "triply convergent" chemical step. In other words, this step comprises formation of the $C_{12}$–$C_{13}$ bond and the $C_7$–$C_8$ bond in the molecule by the sequential addition of the easily available reagents 4 and 5 to produce a suitably activated optically active cyclopentene prostaglandin nucleus.

The following shows structural formulas for the prostaglandin molecules as well as two of the known side chain reagents:

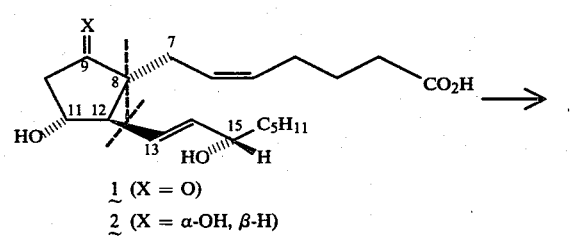

1 (X = O)
2 (X = α-OH, β-H)

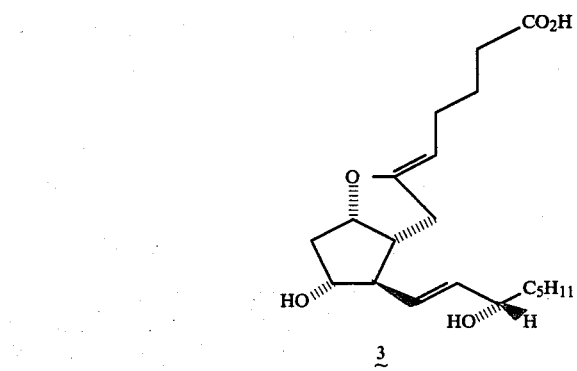

3

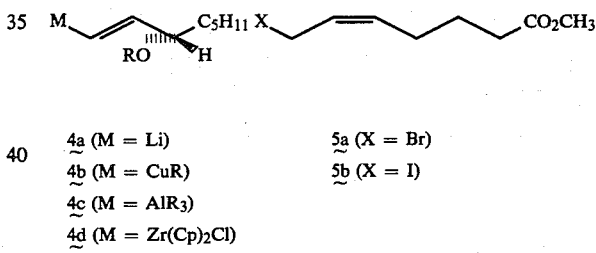

| 4a (M = Li) | 5a (X = Br) |
| 4b (M = CuR) | 5b (X = I) |
| 4c (M = AlR₃) | |
| 4d (M = Zr(Cp)₂Cl) | |

In the past substantial efforts have been made to use 4-alkoxy cyclopent-2-enone 6 as the acceptor for such a conjugate-addition alkylation sequence. Although the conjugate-addition reaction (6+4) has been found to work well, subsequent enolate alkylation with the "upper side chain" reagent 5 is totally unsatisfactory. Presently there are known only indirect procedures for further elaboration of that enolate to prostaglandin $E_2$ (1).

A solution to this problem which has now been developed is by use of chiral vinyl sulfone d-7 as a substrate for the conjugate-addition/alkylation reaction.

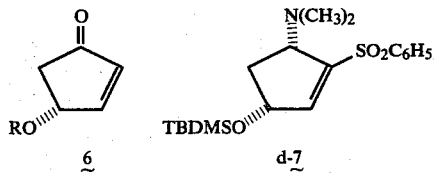

Among the advantages of the various steps and combination of steps which constitute the essential features of the invention is the ready capability to combine chemically and in high yields, three or more separate components or molecular fragments efficiently, thereby constructing optically active prostaglandin nuclei. Such novel processes make possible and commercially practical, the manufacture of optically active prostaglandin homologs and analogs both of known and hitherto unknown structure. The rapidity, reduced number of steps, and efficiency of the processes herein described constitute a substantial portion of the advantages possible in the technology for preparation of a wide variety of prostaglandin analogs.

More particularly, it is now possible, using the newly disclosed process, to prepare optically active PGE$_2$ and PGE$_2$ analogs, which can, as may be desired, or required, be converted to PGF$_2\alpha$ and PGI$_2$ analogs and homologs.

DETAILED DESCRIPTION

Reaction of the optically active sulfide alcohol d-8 with three equivalents of metachloroperbenzoic acid in methylene chloride yields the highly crystalline epoxy-alcohol 9. Treatment of 9 with catalytic diazabicycloundecene (DBU) (to produce the dihydroxy-vinyl-sulfone) followed by in situ silylation of the less hindered alcohol moiety yields the crystalline monosilyl ether 10a. The equation below shows this conversion:

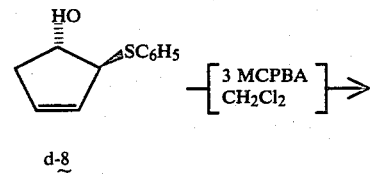

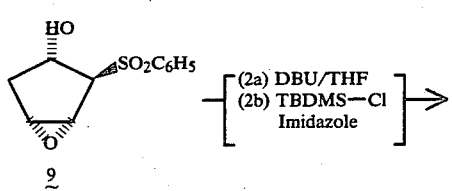

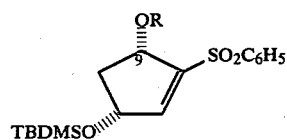

10a (R = H)
10b (R = SO$_2$CH$_3$)

Conversion of 10a (d-7) was readily accomplished by treatment of alcohol 10a with methanesulfonyl chloride and triethylamine in methylene chloride to give allylic mesylate 10b. Although this sensitive material (10b) can be successfully isolated and characterized, it has now been found to be more expedient to use it as an unisolated intermediate and treat a methylene chloride solution of crude mesylate 10b with gaseous dimethyl amine to produce vinyl sulfone 11. Quaternization of 11 with methylfluorosulfonate yielded the crystalline ammonium salt 12 which also was not isolated but was directly treated with gaseous dimethyl amine in methylene chloride to yield the crystalline vinyl sulfone d-7. Use of dimethyl sulfate instead of methylfluorosulfonate in this reaction gives slightly lower yields. The reactions are shown in the equation below:

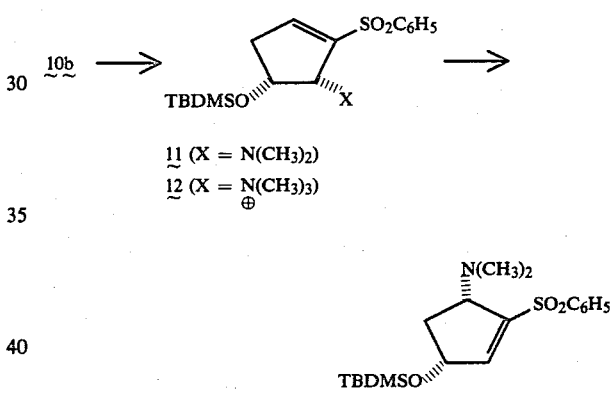

Reaction of vinyl sulfone d-7 with optically active vinyllithium reagent 4a followed by quenching with water yields a 92:5 mixture of 1:1 adducts 13 and 14. Sequential treatment of d-7 with optically active vinyllithium reagent 4a followed by warming and rapid addition of allyl iodide 5b and allowing the reaction mixture to warm further, produced a mixture of products. This mixture is passed through a plug of alumina to remove nonpolar impurities related to the side-chain reagents 4a, 5a and this step is followed by crystallization of the polar fraction from aqueous methanol to afford the crystalline adduct 15. Further analysis of the polar fraction of the reaction residues also reveals the presence of minor amounts of non-alkylated 1:1 adducts 13 and 14. These reactions are summarized by the equations set forth below.

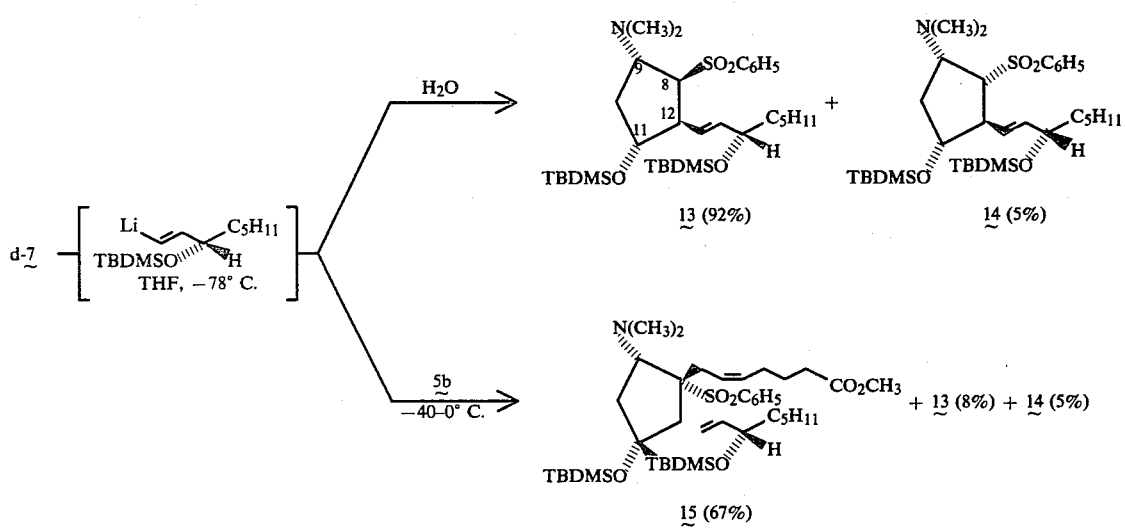

Reaction of 15 with trichloroethyl chloroformate in the presence of solid sodium bicarbonate yields the urethane 16 as an oil. Reduction of 16 with activated zinc in terahydrofuran gives the crystalline secondary amine 17. Hydrolysis of the ester moiety of amine 17 by treatment with sodium hydroxide followed by evaporation of the methanol and extraction of a sodium bicarbonate-buffered solution with ethyl acetate produced amino acid 18 as a yellowish foam. Addition of 40% peracetic acid to a solution of 18 in wet methanol containing solid sodium carbonate and a catalytic amount of sodium tungstate yields the oily α-oximino sulfone 19 after purification by chromatography on silica gel.

Oximino-sulfone 19 is readily desulfonylated by sequential (1) treatment with sodium methoxide to deprotonate the carboxylic acid moiety, (2) followed by treatment with excess sodium borohydride and finally (3) slow introduction of an additional portion of sodium methoxide followed by reaction for an additional 5 hour period at room temperature. Filtration of the crude product through silica gel to remove polar impurities gives the oil oxime 21 as a single C-8 isomer assayed and identified by C-13 NMR. The desulfonylation reaction presumably occurs via 1,4-addition of hydride to the vinyl nitroso intermediate (20) which is produced by the alkali-catalyzed 1,4-elimination of phenylsulfinic acid from the starting α-oximino sulfone 19. The very high stereospecificity observed in this reaction may be a consequence of enhanced α-face shielding afforded by a folded conformation of the hydrophobic alkyl groups of the C-11 silyloxy moiety.

Conversion of oxime 21 to chiral prostaglandin E₂ (1) is accomplished by reaction of 21 with a 1:1 solution of acetone and aqueous formaldehyde in the presence of boron trifluoride as a catalyst. The crude product so produced was purified by extraction of an ether solution with saturated sodium bicarbonate followed by regeneration of the prostaglandin acids by acidifying the aqueous phase with acetic acid. The l(−)PGE₂ (1) product was obtained as an oil after column chromatography on silica gel to remove a small amount of PGA₂(ca 10%). Recrystallization gave crystalline l(−)PGE₂. The identity of l(−)PGE₂ was confirmed by 360 MHz proton NMR, C13-NMR, as well as by direct comparison with an authentic sample.

In summary and considering the enantioconvergent nature of the process for synthesis of chiral dimethylaminovinyl sulfone d7, the overall yield of l(−)PGE₂ 1 from the racemic sulfide alcohol dl-8 is 13% including the step of the resolution process.

This series of reactions to obtain the final desired product is shown by the equations set forth below:

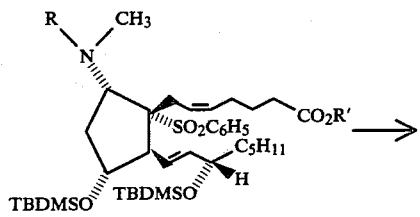

15 (R = R' = CH₃)
16 (R = Cl₃CCH₂OCO, R' = CH₃)
17 (R = H, R' = CH₃)
18 (R = R' = H)

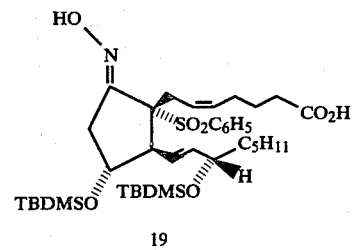

19

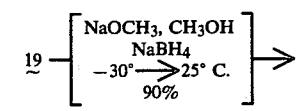

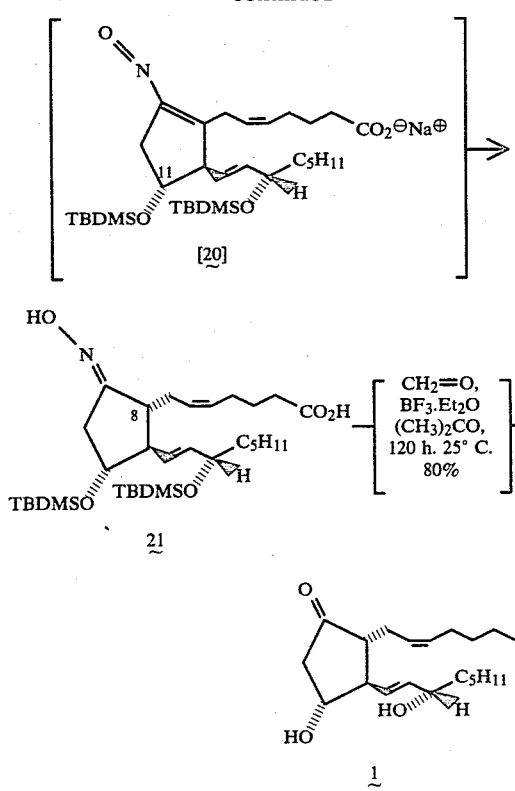

tetrahydrofuran at reflux for 18 hours yields a mixture of bromodiol 27 as well as unreacted diol 25 as assayed by thin layer chromatography. This reaction mixture is cooled and solid phenyl disulfide and bromine are introduced to complete the conversion of diol 25 to bromodiol 27. Bromodiol 27 is quite reactive and can be cyclized to epoxide 29 by treatment with aqueous sodium hydroxide solution.

Purification of the crude epoxide was effected by plug filtration through silica gel to remove excess phenyl disulfide and give the oily epoxide 28. The overall 23→28 transformation is a stereospecific sulfide-directed epoxidation in which the sulfur moiety has been retained in a potentially useful low oxidation state. These conversion steps are shown in the equations below:

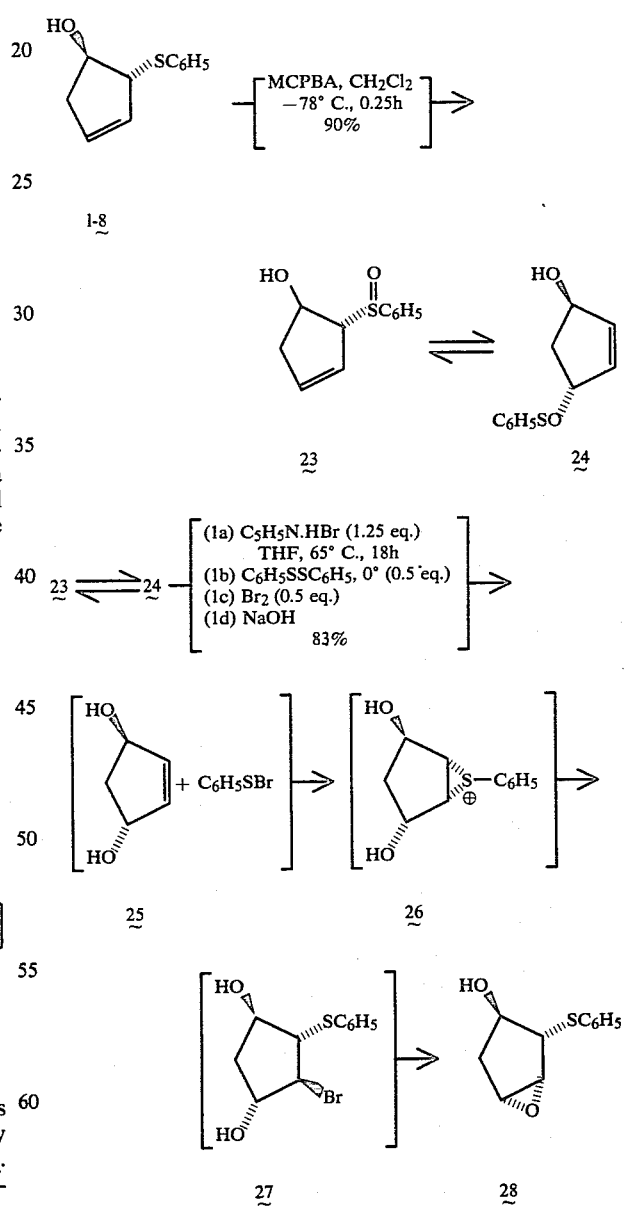

There is above described the conversion of the dextrorotatory sulfide-alcohol d-8 to chiral amino vinyl sulfone d-7. Vinyl sulfone d-7 was used as an operational equivalent of 4-alkoxy-cyclopentenone 22 in a triply-convergent, conjugate-addition/alkylation total synthesis of l(−) prostaglandin E$_2$ (1) according to the following equations:

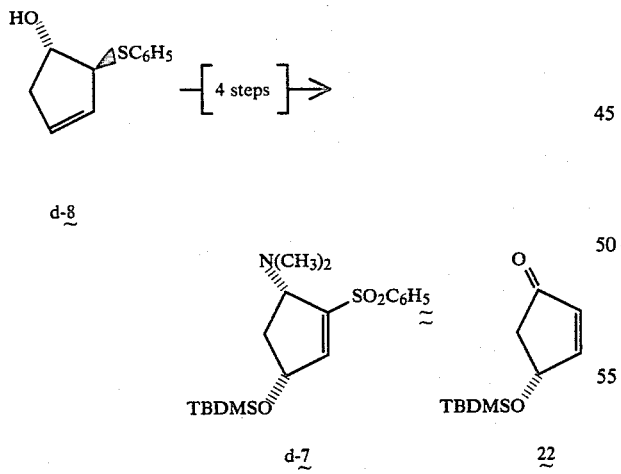

The resolution of racemic sulfide-alcohol dl-8 was done by classical steps and produced approximately equivalent amounts of both enantiomers d-8 and l-8. Conversion of the "unnatural" enantiomer l-8 to prostaglandin precursor d-7 has also been carried out by oxidation of l-8 with one equivalent of meta-chloroperoxybenzoic acid (MCPBA) to give sulfoxide 23 which is in equilibrium with sulfenate ester 24. Treatment of sulfoxide 23 with freshly prepared pyridine hydrobromide in Completion of the enantioconversion process was accomplished by MCPBA oxidation of sulfide 28 to the crystalline sulfone 29. Treatment of sulfone 29 with a catalytic amount of DBU produces a trans-1,4-dihydroxy vinyl sulfone which is monosilylated in situ to yield the highly crystalline hydroxysulfone 30. Alcohol 30 was transformed to mesylate 31. The crude mesylate 31 was not isolated but was directly treated with gaseous dimethyl amine to yield dimethylamino vinyl sulfone 11 which is identical in every property and characteristic to that similarly obtained from cis-mesylate 10b which had been prepared from the "natural" enantiomeric sulfide-alcohol d-8.

It appears that the silyloxy group facilitates a directed addition via intermediate (32) in the polarized SN2' Lawton-type reaction. Conversion of 11 to d-7 was accomplished as described above. Vinyl sulfone d-7 is obtained by this series of steps an overall yield of 46% from the "unnatural" enantiomer l-8.

These reaction steps are shown in the series of equations below:

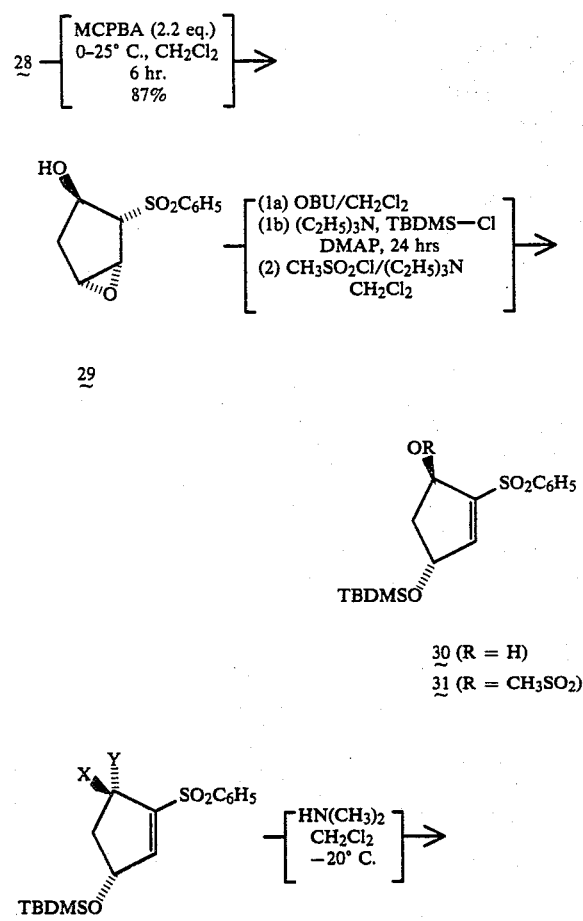

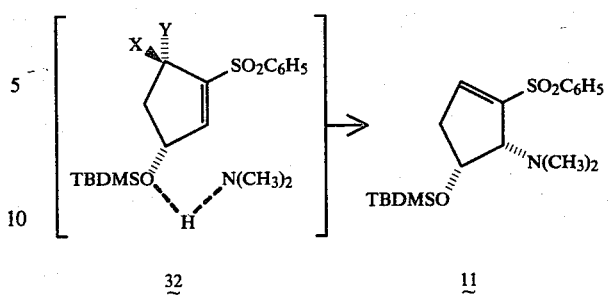

The following Examples are illustrative of typical of the processes, methods and products of the present invention, but are not intended to be construed as strictly limited thereto.

EXAMPLES

Any and all new compounds reported and described herein, were found to exhibit satisfactory 1H-NMR, 13C-NMR, mass and exact mass identification. In the instances where the compounds were crystalline materials, the elemental analyses obtained agreed within experimental error with the calculated values. The yields of isolated and identified products were shown to have greater than 95% purity.

EXAMPLE 1

A reaction of the optically active sulfide alcohol identified as compound d-8 having the properties of mp ca. 28°; $[\alpha]_D^{25} +116°$, c 0.308, CHCl$_3$; 92% ee with an amount corresponding to three equivalents of meta-chloroperbenzoic acid in a reaction medium of methylene chloride yields as the product, the highly crystalline epoxy-alcohol 9 having the properties mp 103°–104° C.; $[\alpha]_D^{25} +64°$, c 0.429, CHCl$_3$; in an 88% yield.

EXAMPLE 2

In the next reaction step, compound 9 is treated with catalytic DBU to produce the dihydroxyvinyl sulfone. This step is followed by in situ silylation of the less hindered alcohol intermediate to yield the crystalline monosilyl ether 10a having the properties mp 72°–73° C.; $[\alpha]_D^{25} +58°$, c 0.456, CHCl$_3$; in a 79% yield.

EXAMPLE 3

In the next reaction step, the alcohol 10a is treated with methane-sulfonyl chloride and triethylamine in methylene chloride as reaction medium. This reaction proceeds smoothly to yield allylic mesylate 10b. Although this sensitive material can be successfully isolated and characterized, it is preferred to treat a methylene chloride solution of crude mesylate 10b with gaseous dimethyl amine at −20° C. for 5 minutes to produce the vinyl sulfone 11 having the properties mp 96°–98° C.; $[\alpha]_D^{25} -18°$, c 0.434, CHCl$_3$. This sulfone is produced in 95% yield. In a next step, the quaternization of 11 with one equivalent of methylfluorosulfonate for 2 hours at 25° C. in CH$_2$Cl$_2$ as reaction medium yielded the crystalline ammonium salt 12. This ammonium salt was also preferably not isolated but was directly treated with gaseous dimethyl amine at −20° in methylene chloride for five minutes to produce a 98% yield of the crystalline vinyl sulfone d-7 having the properties, mp 67°–68° C.; $[\alpha]_D^{25} +153°$, c 0.385, CHCl$_3$. Alternatively, treatment with dimethyl sulfate for 4 days at 24° C. in CH$_2$Cl$_2$ in place of methylfluorosulfonate gave slightly lower yields of about 90%.

EXAMPLE 4

In the next step, the reaction of vinyl sulfone d-7 with an optically active vinyllithium reagent 4a followed by quenching with water yielded a 92:5 mixture of 1:1 adducts 13 and 14. The sequential treatment of 28.6 g. (75 mmole) of d-7 with in tetrahydrofuran (THF), with 1.1 eq. of optically active vinyllithium reagent 4a at −78° C. followed by warming to −40° and rapid addition of 1.1 equivalents as an 0.5 M THF solution of allyl iodide 5b and allowing the reaction mixture to warm to 0° C. over the course of one hour yielded a mixture of products. This mixture was passed through a plug of alumina to remove nonpolar impurities related to the side-chain reagents 4a and 5b. After crystallization of the polar fraction from aqueous methanol there was obtained 38.7 g. (a 67% yield) of the crystalline adduct 15 having the properties; mp 60°-62°; $[\alpha]_D^{25}$ −20.0°, c 0.429, CHCl$_3$. A further examination of the polar fraction of the reaction residues showed the presence of minor amounts of the non-alkylated 1:1 adducts 13 and 14.

EXAMPLE 5

In the next step, the reaction of 15 with 2 equivalents of trichloroethyl chloroformate at 25° C. for 72 hours in the presence of solid sodium bicarbonate yields the urethane 16 as an oil in 96% yield.

EXAMPLE 6

The reduction of 16 with activated zinc in tetrahydrofuran was then carried out to give the crystalline secondary amine 17 in 92% yield and having the properties, mp 50°-52° C.; $[\alpha]_D^{25}$ −6.2°, c 0.431, CHCl$_3$.

EXAMPLE 7

The ester moiety of intermediate amine 17 was hydrolyzed by treatment with sodium hydroxide (3 eq.) in 2% aqueous methanol for 48 hours at 25° C., followed by evaporation of the methanol and extraction of its sodium bicarbonate-buffered solution with ethyl acetate. The product, amino acid 18, was isolated as a yellowish foam (99%). The addition of 6 equivalents of 40% peracetic acid to a solution of 18 in wet methanol containing 15 equivalents of solid sodium carbonate and a catalytic amount of sodium tungstate gave an 85% yield of the oily α-oximino sulfone 19 after purification by chromatography on silica gel.

EXAMPLE 8

The oximino-sulfone 19 was readily desulfonylated by sequential treatment with 1 equivalent of sodium methoxide at −30° C. in methanol to deprotonate the carboxylic acid moiety. This step was followed by an addition of an excess (16 hydride equivalents) of sodium borohydride and warming to 25° C. This was followed by a slow introduction over a period of one hour of an additional portion of 1.2 equivalent of sodium methoxide in methanol and followed by reaction for an additional 5 hrs. at room temperature. Filtration of the crude product through silica gel to remove polar impurities gives a 90% yield of the oily oxime 21 as a single C-8 isomer as assayed by C-13 NMR.

EXAMPLE 9

The conversion of oxime 21 to chiral prostaglandin E$_2$ (1) is carried out by reacting 14.15 g. (25 mmole) of 21 with a 1:1 solution of acetone and aqueous 40% formaldehyde in the presence of 0.7 eq. of boron trifluoride as a catalyst for 5 days at 25° C. The crude product was purified by extraction of an ether solution with saturated sodium bicarbonate followed by regeneration of the prostaglandin acids by acidifying the aqueous phase with acetic acid to pH 5.5 after removal of the ether-soluble paraformaldehyde residues. A yield of 6.69 g. (80%) of the l(−) PGE$_2$ (1) was obtained as an oil after column chromatography on silica gel to remove a small amount of PGA$_2$ (ca 10%).

Recrystallization from ethyl acetate/hexane gave crystalline PGE$_2$ having the properties, mp 64°-66° C.; $[\alpha]_D^{25}$ −64°, c 1.03, THF). The identity of PGE$_2$ (1) was confirmed by 360 MHZ proton NMR, C13-NMR, as well as by direct comparison with an authentic sample. The overall yield of l(−), PGE$_2$(l) from chiral vinyl sulfone d-7 was 36% when the product was prepared by this sequence of steps.

EXAMPLE 10

An alternative procedure for converting the enantiomeric sulfide-alcohol l-8 to prostaglandin precursor d-7 can be carried out by oxidation of l-8 with one equivalent of meta-chloroperoxybenzoic acid to produce sulfoxide 23, a compound which is known to be in equilibrium with sulfenate ester 24. Treatment of 19.6 g. (94 mmole) of 23 with 1.25 equivalents, a 10% mol % excess in pyridine, with freshly prepared pyridine hydrobromide in tetrahydrofuran at reflux for 18 hours produced a mixture of bromodiol 27 as well as unreacted diol 25 as assayed by thin layer chromatography. This reaction mixture was cooled to 0° C. and 50 mmol of solid phenyl disulfide and 50 mmol of bromine were introduced to complete the conversion of diol 25 to bromodiol 27.

Bromodiol 27 as quite sensitive and was cyclized to the epoxide 28 by treatment with aqueous sodium hydroxide solution in the work-up procedure of the sulfenylation sequence step. Purification of the crude epoxide 28 so-produced was effected by plug filtration through silica gel to remove the excess phenyl disulfide and gives 16.3 g. (83% yield) of the oily epoxide 28. To summarize, the overall yield of the 23 to 28 transformation, accomplished in this sequence of steps, is a stereospecific sulfide-directed epoxidation in which the sulfur moiety has been kept in a more potentially useful low oxidation state.

EXAMPLE 11

The enantioconversion process was completed by MCPBA oxidation of sulfide 28 to the crystalline sulfone 29 in 87% yield having the properties mp=103.5°-105° C., $[\alpha]_D^{25}$ = −137°, c 0.437, CHCl$_3$.

EXAMPLE 12

In the next step the sulfone 29 is treated with a catalytic amount of 0.1 equivalent of DBU in CH$_2$Cl$_2$ for 0.5 hour at 25° C. to produce a trans-1,4-dihydroxy vinyl sulfone which is monosilyated in situ with (C$_2$H$_5$)$_3$N/, t-Bu(CH$_3$)$_2$ SiCl/, DMAP (2:1.3:0.2); CH$_2$Cl$_2$ for 24 hours to give a 79% yield of the highly crystalline hydroxysulfone 30 having the properties, mp 76°-77° C.; $[\alpha]_D^{25}$ = +147°, c 0.360 CHCl$_3$. The hydroxysulfone alcohol 30 was transformed to mesylate 31 by the method of Crossland and Servis. The crude mesylate 31 was not isolated but was directly treated with gaseous dimethylamine in methylene chloride at −20° C. for 5 minutes to give dimethylamino vinyl sulfone 11 in 92% yield from 30 and having the properties, mp 94°–95° C.; $[\alpha]_D^{25}$ −17.7°, c 0.434, CHCl$_3$. This product is identical in every respect to that similarly obtained from cis-mesylate 10-b which had been prepared from the "natural" enantiomeric sulfide-alcohol d-8.

EXAMPLE 13

Conversion of 11 to d-7 in 98% yield was accomplished as described in Example 3 above, thus producing an overall yield of 46% from the "unnatural" enantimoer 1-8.

What is claimed is:
1. (1S,2R,3R,4R)-Cis-3,4-epoxy-trans-2-(phenylsulfonyl)-cyclopentan-1-ol.
2. (1R,2S,3R,4R)-Trans-3,4-epoxy-trans-2-(phenylsulfonyl)-cyclopentan-1-ol.

* * * * *